(12) United States Patent
Inagaki et al.

(10) Patent No.: US 10,278,985 B2
(45) Date of Patent: May 7, 2019

(54) AQUEOUS OPHTHALMIC SOLUTION

(71) Applicant: SANTEN PHARMACEUTICAL CO., LTD., Osaka-shi, Osaka (JP)

(72) Inventors: Koji Inagaki, Ikoma (JP); Naoki Matsumoto, Ikoma (JP); Toshihiro Ogawa, Ikoma (JP); Yukihisa Wakabayashi, Ikoma (JP); Asuka Kamimura, Ikoma (JP); Yoshihiro Oshita, Ikoma (JP); Hitoshi Nakazawa, Ikoma (JP); Isao Matsuoka, Ikoma (JP)

(73) Assignee: SANTEN PHARMACEUTICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/539,283

(22) PCT Filed: Dec. 25, 2015

(86) PCT No.: PCT/JP2015/086230
§ 371 (c)(1),
(2) Date: Jun. 23, 2017

(87) PCT Pub. No.: WO2016/104704
PCT Pub. Date: Jun. 30, 2016

(65) Prior Publication Data
US 2017/0348344 A1    Dec. 7, 2017

(30) Foreign Application Priority Data

Dec. 25, 2014 (JP) ................. 2014-263003
Jun. 5, 2015 (JP) ................. 2015-114595

(51) Int. Cl.
| | | |
|---|---|---|
| *A61K 31/7084* | (2006.01) | |
| *A61K 47/18* | (2017.01) | |
| *A61K 9/08* | (2006.01) | |
| *G02C 13/00* | (2006.01) | |
| *A61K 9/00* | (2006.01) | |
| *A61K 47/24* | (2006.01) | |
| *A61K 31/155* | (2006.01) | |

(52) U.S. Cl.
CPC ........ *A61K 31/7084* (2013.01); *A61K 9/0048* (2013.01); *A61K 9/08* (2013.01); *A61K 31/155* (2013.01); *A61K 47/18* (2013.01); *A61K 47/24* (2013.01); *G02C 13/00* (2013.01)

(58) Field of Classification Search
CPC ...... A61K 31/7084; A61K 9/08; A61K 47/18; G02C 13/00
USPC ........................... 424/489; 514/51
See application file for complete search history.

(56) References Cited

U.S. PATENT DOCUMENTS

2014/0221306 A1 * 8/2014 Sakatani ............ A61K 31/7084
                                                                 514/51
2015/0072951 A1    3/2015 Sakatani et al.

FOREIGN PATENT DOCUMENTS

| JP | 09-301858 A | 11/1997 |
|---|---|---|
| JP | 11-060505 A | 3/1999 |
| JP | 2009-073788 A | 4/2009 |
| JP | 2010-106015 A | 5/2010 |
| JP | 2011-051982 A | 3/2011 |
| JP | 2012-062269 A | 3/2012 |
| JP | WO 2012/090994 | * 7/2012 |
| JP | 2013-227291 A | 11/2013 |
| WO | WO 2011/016562 A1 | 2/2011 |
| WO | WO 2013/146649 A1 | 10/2013 |

OTHER PUBLICATIONS

International Search Report (PCT/ISA/210) dated Feb. 23, 2016, by the Japanese Patent Office as the International Searching Authority for International Application No. PCT/JP2015/086230.
Written Opinion (PCT/ISA/237) dated Feb. 23, 2016, by the Japanese Patent Office as the International Searching Authority for International Application No. PCT/JP2015/086230.
Office action dated Dec. 27, 2016 for Japanese patent application No. 2016-111473 and English translation thereof.
(Notice of results of Preliminary Examination dated Jul. 19, 2017 for Korean patent application No. 10-2017-7014598 and English translation thereof.
Fukada et al., "Cytotoxic Effect of Hyaluronate Sodium Ophthalmic Solution on Cultured Rabbit Corneal Cell Line", The Journal of Medicine, 2006, vol. 56, No. 3, pp. 385 to 388 and English translation thereof.
Burstein, "Preservative cytotoxic threshold for benzalkonium chloride and chlorhexidine digluconate in cat and rabbit corneas", Investigative Ophthalmology & Visual Science, 1980, p. 308-313, vol. 19, No. 3.
Burstein, "The effects of topical drugs and preservatives on the tears and corneal epithelium in dry eye", Transactions of the ophthalmological societies of the United Kingdom, 1985, p. 402-409, vol. 104, Pt.4.
Duncan et al, "Some preservatives in eyedrop preparations hasten the formation of dryspots in the rabbit cornea", British Journal of Pharmacology, 1976, pp. 359P-360P, vol. 56, No. 3.
Handbook of Pharmaceutical Excipients Fifth Edition, Yakuji Nippo Ltd., Feb. 28, 2007, pp. 283-289 and English translation thereof.

* cited by examiner

*Primary Examiner* — Yih-Horng Shiao
(74) *Attorney, Agent, or Firm* — Buchanan, Ingersoll & Rooney PC (57) ABSTRACT

Provided is an aqueous ophthalmic solution comprising diquafosol or a salt thereof at a concentration of 0.1% to 10% (w/v) and a chlorhexidine at a concentration of 0.0001% to 0.1% (w/v).

12 Claims, 1 Drawing Sheet

AQUEOUS OPHTHALMIC SOLUTION

TECHNICAL FIELD

The present invention relates to an aqueous ophthalmic solution comprising diquafosol or a salt thereof at a concentration of 0.1% to 10% (w/v) (to also be referred to as diquafosol ophthalmic solution), which also comprises a chlorhexidine at a concentration of 0.0001% to 0.1% (w/v).

BACKGROUND ART

Ophthalmic solutions typically consist of types that are used multiple times over a fixed period of time after opening (multi-dose type ophthalmic solutions) and types that are used only once (unit-dose type ophthalmic solutions). In particular, multi-dose type ophthalmic solutions typically comprise preservatives to prevent decomposition of the product due to microbial contamination during use and ensure preservation stability.

Benzalkonium chloride (to also be referred to as BAK) is commonly used as a preservative that has superior preservative effects. On the other hand, the use of BAK at a high concentration is known to have the potential to cause corneal disorders. In addition, if a user applies an ophthalmic solution comprising BAK while wearing soft contact lenses, BAK has been indicated to have a detrimental effect on the soft contact lenses such as by causing deformation thereof as a result of making contact therewith. Consequently, the application of an ophthalmic solution comprising BAK is normally prohibited when wearing soft contact lenses.

Diquafosol is a purine receptor agonist, also referred to as $P^1,P^4$-di(uridine-5')tetraphosphate or $Up_4U$, that is used for the treatment of dry eye in Japan in the form of an ophthalmic solution comprising diquafosol sodium at a concentration of 3% (w/v) (trade name: Diquas® Ophthalmic Solution 3%). This Diquas® Ophthalmic Solution 3% comprises BAK for the reason indicated above.

In addition, Patent Document 1 discloses an aqueous ophthalmic solution comprising diquafosol or a salt thereof at a concentration of 0.1% to 10% (w/v) and a chelating agent at a concentration of 0.0001% to 1% (w/v).

PRIOR ART DOCUMENTS

Patent Documents

[Patent Document 1] Japanese Unexamined Patent Application Publication No. 2013-227291

DISCLOSURE OF THE INVENTION

Problems to be Solved by the Invention

An object of the present invention is to provide a diquafosol ophthalmic solution that demonstrates a higher degree of safety without comprising BAK.

Means for Solving the Problems

As a result of conducting extensive studies to solve the aforementioned problems, the inventors of the present invention found that an aqueous ophthalmic solution comprising diquafosol or a salt thereof at a concentration of 0.1% to 10% (w/v) and a chlorhexidine at a concentration of 0.0001% to 0.1% (w/v) (to be referred to as the present ophthalmic solution) has superior preservative effects, thereby leading to completion of the present invention. Moreover, the inventors of the present invention found that the present ophthalmic solution prevents deformation of a soft contact lens. In addition, the inventors of the present invention found that the present ophthalmic solution demonstrates a higher level of cell viability in cultured immortalized human corneal epithelial cells than ophthalmic solutions comprising BAK and ophthalmic solutions comprising chlorhexidine but not comprising diquafosol or a salt thereof. In addition, the inventors of the present invention found that the present ophthalmic solution significantly increases non-invasive tear break up time (NIBUT) in an eye wearing a soft contact lens, or in other words, stabilizes the tear film in an eye wearing a soft contact lens. On the other hand, such effects have not been observed with artificial tear solutions. Since the onset and/or exacerbation of dry eye symptoms caused by wearing soft contact lenses are attributable to a decrease in tear film stability, stabilization of the tear film by the present ophthalmic solution is useful for the prevention and/or treatment of dry eye in an eye wearing a soft contact lens. In addition, the present ophthalmic solution is also useful for the prevention and/or treatment of eye dryness and/or eye discomfort in an eye wearing a soft contact lens.

Namely, the present invention provides an aqueous ophthalmic solution as indicated below.

(1) An aqueous ophthalmic solution comprising diquafosol or a salt thereof at a concentration of 0.1% to 10% (w/v) and a chlorhexidine at a concentration of 0.0001% to 0.1% (w/v).

(2) The aqueous ophthalmic solution described in (1), wherein the chlorhexidine is chlorhexidine gluconate.

(3) The aqueous ophthalmic solution described in (1) or (2), wherein the concentration of the chlorhexidine in the ophthalmic solution is 0.0005% to 0.05% (w/v).

(4) The aqueous ophthalmic solution described in (1) or (2), wherein the concentration of the chlorhexidine in the ophthalmic solution is 0.001% to 0.005% (w/v).

(5) The aqueous ophthalmic solution described in any of (1) to (4), wherein the concentration of diquafosol or a salt thereof in the ophthalmic solution is 3% (w/v).

(6) The aqueous ophthalmic solution described in any of (1) to (5), further comprising a chelating agent.

(7) The aqueous ophthalmic solution described in (6), wherein the chelating agent is edetic acid or a salt thereof.

(8) The aqueous ophthalmic solution described in any of (1) to (7), which is for a soft contact lens.

(9) The aqueous ophthalmic solution described in (8), wherein the soft contact lens is a silicone hydrogel contact lens.

In addition, the present invention provides a method for preventing deformation of a soft contact lens as indicated below.

(10) A method for preventing deformation of a soft contact lens with the aqueous ophthalmic solution described in any of (1) to (7).

Moreover, the present invention also relates to that indicated below.

(11) An aqueous ophthalmic solution for the prevention and/or treatment of dry eye comprising diquafosol or a salt thereof at a concentration of 0.1% to 10% (w/v) and a chlorhexidine at a concentration of 0.0001% to 0.1% (w/v).

(12) A use of an aqueous ophthalmic solution comprising diquafosol or a salt thereof at a concentration of 0.1% to 10% (w/v) and a chlorhexidine at a concentration of 0.0001% to 0.1% (w/v) for the prevention and/or treatment of dry eye.

(13) A method for the prevention and/or treatment of dry eye, comprising the application of an aqueous ophthalmic solution comprising diquafosol or a salt thereof at a concentration of 0.1% to 10% (w/v) and a chlorhexidine at a concentration of 0.0001% to 0.1% (w/v).

In addition, the present invention provides the aqueous ophthalmic solutions indicated below.

(14) The aqueous ophthalmic solution described in any of (1) to (7) for the prevention and/or treatment of dry eye in an eye wearing a soft contact lens.

(15) The aqueous ophthalmic solution described in any of (1) to (7) for improving tear film stability in an eye wearing a soft contact lens.

(16) The aqueous ophthalmic solution described in any of (1) to (7) for the prevention or treatment of eye dryness or eye discomfort in an eye wearing a soft contact lens.

(17) The aqueous ophthalmic solution described in any of (14) to (16), wherein the soft contact lens is a silicone hydrogel contact lens.

Effects of the Invention

As is clear from the results of test examples to be subsequently described, the present ophthalmic solution has superior preservative effects. Moreover, since the present ophthalmic solution prevents deformation of a soft contact lens, it can be used for a soft contact lens. In addition, the present ophthalmic solution demonstrates a higher level of cell viability in cultured immortalized human corneal epithelial cells than ophthalmic solutions comprising BAK or ophthalmic solutions comprising chlorhexidine but not comprising diquafosol or a salt thereof. Accordingly, the present ophthalmic solution demonstrates higher safety with respect to a living body, and particularly keratoconjunctival epithelium, and is useful for use in diseases such as dry eye in which the keratoconjunctival epithelium is unstable. In addition, the present ophthalmic solution significantly increases NIBUT in an eye wearing a soft contact lens. On the other hand, such effects are not observed with artificial tear solutions. Namely, the present ophthalmic solution stabilizes the tear film in an eye wearing a soft contact lens. Since the onset and/or exacerbation of dry eye symptoms caused by wearing soft contact lenses is attributable to a decrease in tear film stability, stabilization of the tear film by the present ophthalmic solution is useful for the prevention and/or treatment of dry eye in an eye wearing a soft contact lens. In addition, the present ophthalmic solution is also useful for the prevention and/or treatment of eye dryness and/or eye discomfort in an eye wearing a soft contact lens.

DESCRIPTION OF THE EMBODIMENTS

The following provides a more detailed explanation of the present invention.

Diquafosol is a compound represented by the chemical structural formula indicated below.

[Chemical 1]

There are no particular limitations on the diquafosol salt provided it is a salt that is acceptable for use as a pharmaceutical, and examples thereof include metal salts such as lithium, sodium, potassium, calcium, magnesium or zinc salt, salts of an inorganic acid such as hydrochloric acid, hydrobromic acid, hydroiodic acid, nitric acid, sulfuric acid or phosphoric acid, salts of an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate ester, methyl sulfate, naphthalenesulfonic acid or sulfosalicylic acid, quaternary ammonium salts such as methyl bromide or methyl iodide, salts of a halogen ion such as bromine ion, chlorine ion or iodine ion, salts of ammonia, and salts of an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine.

In the present invention, hydrates and organic solvates of diquafosol (free form) or a salt thereof are included in the diquafosol or a salt thereof.

In the case diquafosol or a salt thereof has crystal polymorphism and crystal polymorphic groups (crystal polymorphic systems), these crystal polymorphs and crystal polymorphic groups (crystal polymorphic systems) are also included in the scope of the present invention. Here, a crystal polymorphic group (crystal polymorphic system) refers to individual crystalline forms at each stage in the case of undergoing a change in crystalline form according to conditions and state, such as with respect to crystal production, crystallization, or storage and the like, as well as the entire process thereof.

The diquafosol or a salt thereof of the present invention is preferably a sodium salt of diquafosol, and is particularly preferably a diquafosol tetrasodium salt (herein after, also be simply referred to as "diquafosol sodium") represented by the chemical structural formula indicated below.

[Chemical 2]

Diquafosol or a salt thereof can be produced according to, for example, the method disclosed in Japanese Translation of PCT International Application Publication No. 2001-510484.

Although the present ophthalmic solution can also comprise an active ingredient other than diquafosol or a salt thereof, it preferably comprises diquafosol or a salt thereof as the only active ingredient thereof.

Although the concentration of diquafosol or a salt thereof in the present ophthalmic solution is 0.1% to 10% (w/v), it is preferably 1% to 10% (w/v) and particularly preferably 3% (w/v).

In the present invention, an aqueous ophthalmic solution refers to an ophthalmic solution that uses water as a solvent (base).

In the present invention, a chlorhexidine includes chlorhexidine and salts thereof. Chlorhexidine is a compound represented by the following chemical structural formula that is also referred to as 1,1'-hexamethylenebis [5-(4-chlorophenyl)biguanide].

In the present invention, among the aforementioned chlorhexidines, there are no particular limitations on the chlorhexidine salt provided it is a salt that is acceptable for use as a pharmaceutical, and specific examples thereof include organic acid salts [such as monocarboxylates (such as acetates, trifluoroacetates, butyrates, palmitates or stearates), polycarboxylates (such as fumarates, maleates, succinates or malonates), oxycarboxylates (such as gluconates, lactates, tartrates or citrates), and organic sulfonates (such as methanesulfonates, toluenesulfonates or tosylates)], inorganic acid salts (such as hydrochlorides, sulfates, nitrates, hydrobromides or phosphates), salts of organic bases (such as salts of organic amines such as methyl amine, triethylamine, triethanolamine, morpholine, piperazine, pyrrolidone, tripyridine or picoline), and salts of inorganic bases [such as ammonium salts, alkaline metals (such as sodium or potassium), alkaline earth metals (such as calcium or magnesium) or metals such as aluminum]. Among these salts, organic acid salts and/or inorganic acid salts are preferable, oxycarboxylates, monocarboxylates and/or inorganic acid salts are more preferable, gluconates, acetates and/or hydrochlorides are even more preferable, and gluconates are particularly preferable. One type of these chlorhexidine salts may be used alone or two or more types may be arbitrarily combined and used.

Chlorhexidine and salts thereof may be synthesized according to a known method and can be acquired in the form of commercially available products.

Although the concentration of chlorhexidine in the present ophthalmic solution is 0.0001% to 0.1% (w/v), it is preferably 0.0005% to 0.05% (w/v) and particularly preferably 0.001% to 0.005% (w/v).

In the present invention, there are no particular limitations on the "chelating agent" provided it is a compound that chelates metal ions, and examples thereof include edetic acid or a salt thereof such as edetic acid (ethylenediamine tetraacetic acid), monosodium edetate, disodium edetate, trisodium edetate or tetrasodium edetate, dipotassium edetate, tripotassium edetate, tetrapotassium edetate, citric acid or a salt thereof such as citric acid, monosodium citrate, disodium citrate, trisodium citrate, monopotassium citrate, dipotassium citrate or tripotassium citrate, metaphosphoric acid or a salt thereof such as metaphosphoric acid, sodium metaphosphate or potassium metaphosphate, pyrophosphoric acid or a salt thereof such as pyrophosphoric acid, tetrasodium pyrophosphate or tetrapotassium pyrophosphate, polyphosphoric acid or a salt thereof such as polyphosphoric acid, sodium polyphosphate or potassium polyphosphate, malic acid or a salt thereof such as monosodium malate, disodium malate, monopotassium malate or dipotassium malate, tartaric acid or a salt thereof such as sodium tartrate, potassium tartrate or potassium sodium tartrate, and phytic acid or a salt thereof such as sodium phytate or

[Chemical 3]

potassium phytate. Furthermore, in the present invention, edetic acid, citric acid, metaphosphoric acid, pyrophosphoric acid, polyphosphoric acid, malic acid, tartaric acid, phytic acid and salts thereof include hydrates and organic solvates of their respective free forms or salts thereof.

In the present invention, the chelating agent is preferably edetic acid, a salt of edetic acid (edetate), citric acid, a salt of citric acid (citrate), metaphosphoric acid, a salt of metaphosphoric acid (metaphosphate), polyphosphoric acid or a salt of polyphosphoric acid (polyphosphate), and is particularly preferably a sodium salt of edetic acid (including hydrates such as disodium edetate hydrate), citric acid (including hydrates such as citric acid monohydrate), a sodium salt of metaphosphoric acid (sodium metaphosphate) or a sodium salt of polyphosphoric acid (sodium polyphosphate).

In the present invention, the salt of edetic acid is most preferably disodium edetate hydrate (to also be simply referred to as "sodium edetate hydrate").

In addition, one type of these chelating agents may be used alone or two or more types may be arbitrarily combined and used.

Although the concentration of chelating agent in the present ophthalmic solution is, for example, 0.0001% to 1% (w/v), it is preferably 0.0005% to 0.5% (w/v) and particularly preferably 0.001% to 0.1% (w/v).

A nonionic surfactant can be incorporated in the aqueous ophthalmic solution of the present invention as necessary. There are no particular limitations on the nonionic surfactant provided it is within the scope of that which is allowed as a pharmaceutical, and examples thereof include polyoxyethylene fatty acid esters, polyoxyethylene sorbitan fatty acid esters, polyoxyethylene castor oil derivatives, polyoxyethylene polyoxypropylene glycols and sucrose fatty acid esters. Examples of polyoxyethylene fatty acid esters include polyoxyl 40 stearate, examples of polyoxyethylene sorbitan fatty acid esters include Polysorbate 80, Polysorbate 60, Polysorbate 40, polyoxyethylene sorbitan monolaurate, polyoxyethylene sorbitan trioleate and Polysorbate 65, examples of polyoxyethylene castor oil derivatives include polyoxyethylene (10) hydrogenated castor oil, polyoxyethylene (40) hydrogenated castor oil, polyoxyethylene (50) hydrogenated castor oil, polyoxyethylene (60) hydrogenated castor oil, polyoxyl 5 castor oil, polyoxyl 9 castor oil, polyoxyl 15 castor oil, polyoxyl 35 castor oil and polyoxyl 40 castor oil, and examples of polyoxyethylene polyoxypropylene glycols include polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol and polyoxyethylene (20) polyoxypropylene (20) glycol.

In the present invention, an example of the nonionic surfactant is a polyoxyethylene sorbitan fatty acid ester, and is preferably Polysorbate 80, Polysorbate 60, Polysorbate 40, polyoxyethylene sorbitan monolaurate, polyoxyethylene sorbitan trioleate or Polysorbate 65, and particularly preferably Polysorbate 80.

In addition, one type of these nonionic surfactants may be used alone or two or more types may be arbitrarily combined and used.

Although the concentration of nonionic surfactant in the present ophthalmic solution is, for example, 0.0001% to 10% (w/v), it is preferably 0.0005% to 1% (w/v) and particularly preferably 0.0005% to 0.1% (w/v).

A pharmaceutically acceptable additive can be added to the present ophthalmic solution as necessary using commonly used technology, and for example, buffering agents such as sodium phosphate, sodium hydrogen phosphate, sodium dihydrogen phosphate, sodium acetate or c-aminocaproic acid, or isotonic agents such as sodium chloride, potassium chloride or concentrated glycerin, can be selected and added as necessary.

Although the pH of the present ophthalmic solution is only required to be within a range allowed for ophthalmic preparations, normally it is preferably within the range of 4 to 8. A pH adjuster such as hydrochloric acid or sodium hydroxide can be suitably added to the present ophthalmic solution.

The present ophthalmic solution can also be used when wearing a soft contact lens as an ophthalmic solution for a soft contact lens. Examples of soft contact lenses include contact lenses having hydroxyethyl methacrylate for the main component thereof and silicone hydrogel contact lenses.

There are no particular limitations on the type of soft contact lens targeted for application of the present ophthalmic solution, and may be ionic or nonionic or hydrous or non-hydrous soft contact lenses. For example, the present ophthalmic solution can be applied to repeatedly usable contact lenses, one-day disposable contact lenses, one-week disposable contact lenses, two-week disposable contact lenses and all other soft contact lenses currently available on the market or soft contact lenses to be available on the market in the future.

Although usage of the present ophthalmic solution can be suitably altered corresponding to the dosage form, severity of symptoms, age and body weight of the patient to which it is to be administered, and the discretion of the physician, in the case of, for example, having selected eye drops for the dosage form, the eye drops are administered locally to the eyes 1 to 10 times per day, preferably 2 to 8 times per day and more preferably 4 to 6 times per day.

Dry eye is defined as a chronic disease of the tears and keratoconjunctival epithelium caused by various factors that is associated with eye discomfort and vision disorders, and keratoconjunctivitis sicca (KCS) is included in dry eye. In the present invention, the onset of symptoms of dry eye caused by wearing soft contact lenses is included in dry eye.

Symptoms of dry eye include subjective symptoms such as eye dryness, eye discomfort, eye fatigue, heavy eyes, photophobia, eye pain or blurred vision (blearcness), as well as objective symptoms such as hyperemia or keratoconjunctival epithelial disorders.

Although there are many aspects of the cause of dry eye that are unclear, reported examples of causes thereof include Sjogren's syndrome; congenital alacrima; sarcoidosis; graft versus host disease (GVHD) associated with bone marrow transplantation; ocular pemphigoid; Stevens-Johnson syndrome; lacrimal duct obstruction caused by trachoma or the like; diabetes; the decrease in reflex tear secretion caused by corneal refractive surgery (laser-assisted in situ keratomileusis (LASIK)) or the like; Meibomian gland dysfunction; oily layer reduction caused by blepharitis or the like; incomplete winking or incomplete eyelid closure caused byexophthalmos, lagophthalmos or the like; the decrease in the secretion of mucin from a goblet cell; visual display terminal (VDT) work, and so on.

The present ophthalmic solution can be used for the prevention and/or treatment of dry eye.

In the present invention, the prevention and/or treatment of dry eye is defined as the prevention and/or treatment or amelioration of the pathological symptoms and/or findings associated with dry eye, and refers to not only the prevention and/or treatment or amelioration of subjective symptoms such as eye dryness, eye discomfort, eye fatigue, heavy eyes, photophobia, eye pain or blurred vision (blearcness), which are associated with dry eye, but also includes the prevention and/or treatment or amelioration of hyperemia associated with dry eye, keratoconjunctival epithelial disorders or the like. In addition, the prevention and/or treatment of dry eye includes the prevention and/or treatment or amelioration of dry eye symptoms by improving tear film stability in an eye wearing a soft contact lens. Furthermore, the prevention and/or treatment or amelioration of dry eye symptoms refers to the prevention and/or treatment or amelioration of dry eye symptoms derived from exacerbation resulting from the wearing of soft contact lenses by a patient with dry eye, and the prevention and/or treatment or amelioration of dry eye symptoms derived from the wearing of soft contact lenses per se.

In the present invention, improvement of tear film stability refers to qualitative or quantitative improvement of lacrimal fluid. Furthermore, tear film stability can be confirmed by measuring tear break up time (BUT). BUT measured in a more natural state without applying a load in the form of a dye solution and the like is referred to as non-invasive tear break up time (NIBUT).

In the present invention, the prevention and/or treatment of eye dryness or eye discomfort in an eye wearing a soft contact lens refers to the prevention or treatment of eye dryness or eye discomfort associated with destabilization of the tear film caused by wearing soft contact lenses or the prevention or treatment of eye dryness or eye discomfort caused by keratoconjunctival epithelial disorders attributable to the aforementioned destabilization.

Furthermore, CL is the abbreviation for contact lenses while SCL is the abbreviation for soft contact lenses.

Test Example 1

Preservative Effectiveness Test

A preservative effectiveness test was carried out on Ophthalmic Solutions 1 to 6 having the formulations shown in Table 1.

(Sample Preparation)

Ophthalmic Solution 1:

Ophthalmic Solution 1 was prepared in accordance with the formulation shown in Table 1. More specifically, diquafosol sodium (3 g), sodium hydrogen phosphate hydrate (0.2 g), sodium chloride (0.39 g), potassium chloride (0.15 g), sodium edetate hydrate (0.01 g), Polysorbate 80 (0.0005 g) and chlorhexidine gluconate (0.002 g) were dissolved in water and brought to a final volume of 100 mL followed by the addition of a pH adjuster to adjust to pH 7.2.

Ophthalmic Solutions 2-6:

Each of the ophthalmic solutions of Ophthalmic Solutions 2 to 6 was prepared in the same manner as Ophthalmic Solution 1 in accordance with the formulations shown in Table 1.

TABLE 1

(Units: g/100 ml)

|  | Ophthalmic Solution 1 | Ophthalmic Solution 2 | Ophthalmic Solution 3 | Ophthalmic Solution 4 | Ophthalmic Solution 5 | Ophthalmic Solution 6 |
| --- | --- | --- | --- | --- | --- | --- |
| Diquafosol sodium | 3 | 3 | 3 | 3 | 3 | 3 |
| Sodium hydrogen phosphate hydrate | 0.2 | 0.2 | 0.2 | 0.2 | 0.2 | 0.2 |
| Sodium chloride | 0.39 | 0.39 | 0.39 | 0.39 | 0.39 | 0.39 |
| Potassium chloride | 0.15 | 0.15 | 0.15 | 0.15 | 0.15 | 0.15 |
| Sodium edetate hydrate | 0.01 | 0.01 | 0.01 | 0.01 | 0.007 | 0.01 |
| Polysorbate 80 | 0.0005 | 0.0005 | 0.0005 | — | — | — |
| Chlorhexidine gluconate | 0.002 | 0.0025 | 0.002 | 0.0025 | 0.002 | 0.002 |
| pH | 7.2 | 7.5 | 7.8 | 7.5 | 7.2 | 7.2 |

EXAMPLES

Although the following indicates the results of a preservative effectiveness test, deformation prevention evaluation test of soft contact lenses, cytotoxicity test using corneal epithelial cells and evaluation test of NIBUT increasing effect, these examples are provided for the purpose of enhancing understanding of the present invention, and are not intended to limit the scope of the present invention.

(Test Method)

The preservative effectiveness test was carried out in compliance with the preservative effectiveness test method of the 16th edition of the Japanese Pharmacopoeia. For this test, the following test microorganisms were used: *Escherichia coli* (*E. coli*), *Pseudomonas aeruginosa* (*P. aeruginosa*), *Staphylococcus aureus* (*S. aureus*), *Candida albicans* (*C. albicans*) and *Aspergillus brasiliensis* (*A. brasiliensis*).

(Test Results)

The test results are shown in Table 2.

TABLE 2

|  |  | Ophthalmic Solution 1 | Ophthalmic Solution 2 | Ophthalmic Solution 3 | Ophthalmic Solution 4 | Ophthalmic Solution 5 | Ophthalmic Solution 6 |
| --- | --- | --- | --- | --- | --- | --- | --- |
| *E. coli* | 2 weeks | >4.3 | >5.6 | >4.3 | >5.7 | >4.6 | >4.3 |
|  | 4 weeks | >4.3 | >5.6 | >4.3 | >5.7 | >4.6 | >4.3 |
| *P. aeruginosa* | 2 weeks | >4.7 | >5.8 | >4.7 | >5.6 | >4.6 | >4.7 |
|  | 4 weeks | >4.7 | >5.8 | >4.7 | >5.6 | >4.6 | >4.7 |
| *S. aureus* | 2 weeks | >4.9 | >6.0 | >4.9 | >5.6 | >4.5 | >4.9 |
|  | 4 weeks | >4.9 | >6.0 | >4.9 | >5.6 | >4.5 | >4.9 |
| *C. albicans* | 2 weeks | >4.5 | >5.7 | >4.5 | >5.4 | >4.5 | 4.5 |
|  | 4 weeks | >4.5 | >5.7 | >4.5 | >5.4 | >4.5 | >4.5 |

TABLE 2-continued

|  |  | Ophthalmic Solution 1 | Ophthalmic Solution 2 | Ophthalmic Solution 3 | Ophthalmic Solution 4 | Ophthalmic Solution 5 | Ophthalmic Solution 6 |
|---|---|---|---|---|---|---|---|
| *A. brasiliensis* | 2 weeks | 1.7 | 1.3 | 1.7 | 1.0 | 0.7 | 1.4 |
|  | 4 weeks | 2.4 | 1.7 | 2.5 | 1.7 | 0.9 | 1.5 |
|  | Evaluation (JP) | Acceptable | Acceptable | Acceptable | Acceptable | Acceptable | Acceptable |

Furthermore, the test results of Table 2 indicate the degree to which the number of viable organisms at the time of testing decreased in comparison with the number of inoculated organisms in terms of the log reduction, and a value of "1", for example, indicates that the number of viable organisms at the time of testing decreased by 10%.

As shown in Table 2, Ophthalmic Solutions 1 to 6 were shown to be acceptable based on the preservative effectiveness test standards of the Japanese Pharmacopoeia.

(Discussion)

On the basis of the above results, the present ophthalmic solution was shown to have superior preservative effectiveness.

Test Example 2

Deformation Prevention Evaluation Test of Soft Contact Lenses

The effects on soft contact lenses were examined using Ophthalmic Solution 4.

(Sample Preparation)

Ophthalmic Solution 4 was prepared in the same manner as Ophthalmic Solution 1 in accordance with the formulation shown in Table 1.

(Test Method)

Contact lenses corresponding to Group IV of the FDA classification of contact lenses shown in Table 3 (2-week Acuvue® Contact Lenses) were immersed in Ophthalmic Solution 4 for 24 hours followed by calculating changes in the diameter and base curve before and after immersion to examine whether or not the evaluation criteria shown in the following Table 4 are satisfied. In addition, the properties of each of the contact lenses were observed following completion of testing. Furthermore, the evaluation criteria were established based on the Contact Lens Standards for Vision Correction of Ministerial Notification No. 349 of the Ministry of Health, Labour and Welfare (Oct. 5, 2001).

TABLE 3

| Classification[1] | Properties |
|---|---|
| Group I | Moisture content of less than 50%, nonionic |
| Group II | Moisture content of 50% or more, nonionic |
| Group III | Moisture content of less than 50%, ionic |
| Group IV | Moisture content of 50% or more, ionic |

[1]Classification of the U.S. Food and Drug Administration (FDA)

(Evaluation Criteria)

TABLE 4

| | |
|---|---|
| Diameter | Tolerance of within ±0.20 mm of indicated diameter |
| Base curve | Tolerance of within ±0.20 mm of indicated base curve |
| Properties | Absence of internal air bubbles, impurities, discoloration, surface defects and surface irregularities, presence of smoothly rounded edges |

(Results)

The results are shown in Table 5.

TABLE 5

| Parameter | Result |
|---|---|
| Diameter (mm) | +0.02 |
| Base curve (mm) | +0.02 |
| Properties | No change |
| Evaluation | Satisfied standards |

As shown in Table 5, the contact lens satisfied the evaluation criteria after being immersed for a long period of time. Accordingly, Ophthalmic Solution 4 was shown to prevent deformation of soft contact lenses.

(Discussion)

Based on the above results, since the present ophthalmic solution prevents deformation of soft contact lenses, it can be used for soft contact lenses.

Test Example 3

Cytotoxicity Test Using Corneal Epithelial Cells

A cytotoxicity test using corneal epithelial cells was carried out to examine the effects of the present ophthalmic solution on corneal epithelial cells.

(Sample Preparation)

Ophthalmic Solutions 7, 8, 9 and 10 were prepared in the same manner as Ophthalmic Solution 1 in accordance with the formulations shown in Table 6.

TABLE 6

| (Units: g/100 ml) | | | | |
|---|---|---|---|---|
|  | Ophthalmic Solution 7 | Ophthalmic Solution 8 | Ophthalmic Solution 9 | Ophthalmic Solution 10 |
| Diquafosol sodium | 3 | — | 3 | — |
| Sodium hydrogen phosphate hydrate | 0.2 | 0.2 | 0.2 | 0.2 |
| Sodium chloride | 0.39 | 0.39 | 0.41 | 0.41 |
| Potassium chloride | 0.15 | 0.15 | 0.15 | 0.15 |
| Sodium edetate hydrate | 0.01 | 0.01 | 0.01 | 0.01 |
| Benzalkonium chloride[1] | — | — | 0.002 | 0.002 |
| Chlorhexidine gluconate | 0.0025 | 0.0025 | — | — |
| pH | 7.5 | 7.5 | 7.5 | 7.5 |

[1]BAK, chemical structural formula: $[C_6H_5CH_2N(CH_3)_2C_{12}H_{25}]Cl$ (Test Method)

SV40 immortalized human corneal epithelial cells (HCE-T: Riken, Bioresource Center, Cell No. RCB2280) were inoculated into a 96-well plate ($1 \times 10^4$ cells/well) and cultured for 1 day in D-MEM/F12 medium containing 10% FBS. On the following day, the medium was replaced with Ophthalmic Solution 7, Ophthalmic Solution 8, Ophthalmic Solution 9 or Ophthalmic Solution 10 followed by culturing the aforementioned corneal epithelial cells for 15 minutes. Cell viability (equivalent to absorbance of 490 nm) was measured using a Cell Proliferation Assay Kit (Promega Corp., Catalog No.: G3580).

(Results)

Figure 1:
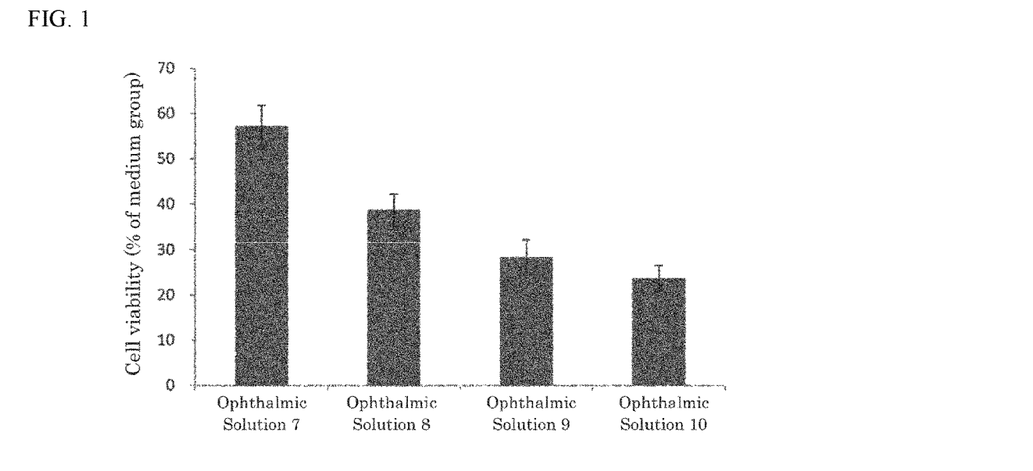
FIG. 1 is a graph showing the results of a cytotoxicity test using corneal epithelial cells in Test Example 3.

The test results are shown in FIG. 1.

As is clear from FIG. 1, the diquafosol ophthalmic solution comprising chlorhexidine gluconate (Ophthalmic Solution 7) demonstrated a higher degree of cell viability in cultured immortalized human corneal epithelial cells than ophthalmic solutions comprising BAK (Ophthalmic Solutions 9 and 10) and the ophthalmic solution comprising chlorhexidine but not comprising diquafosol or a salt thereof (Ophthalmic Solution 8).

(Discussion)

Since the present ophthalmic solution demonstrates a high degree of cell viability in cultured immortalized human corneal epithelial cells, it is highly safe with respect to a living body, and particularly keratoconjunctival epithelium, and is useful for diseases such as dry eye in which the keratoconjunctival epithelium is unstable.

Test Example 4

Evaluation Test of NIBUT Increasing Effect 1

The NIBUT values of a diquafosol ophthalmic solution were examined in eyes in which tear film stability had decreased as a result of wearing soft contact lenses.

(Sample Preparation)

Ophthalmic Solution 4 was prepared in the same manner as Ophthalmic Solution 1 in accordance with the formulation shown in Table 1.

(Test Method)

NIBUT values before and 15, 30, 45 and 60 minutes after applying Ophthalmic Solution 4 (20 μl/eye) were measured for the eyes of cynomolgus monkeys wearing soft contact lenses (product name: Menicon Soft MA®)) with a dry eye observation system (DR-1, Kowa Co., Ltd.). An artificial tear solution (product name: Soft Santia®) was used as a control (N=10 to 11 eyes).

(Results)

Figure 2:
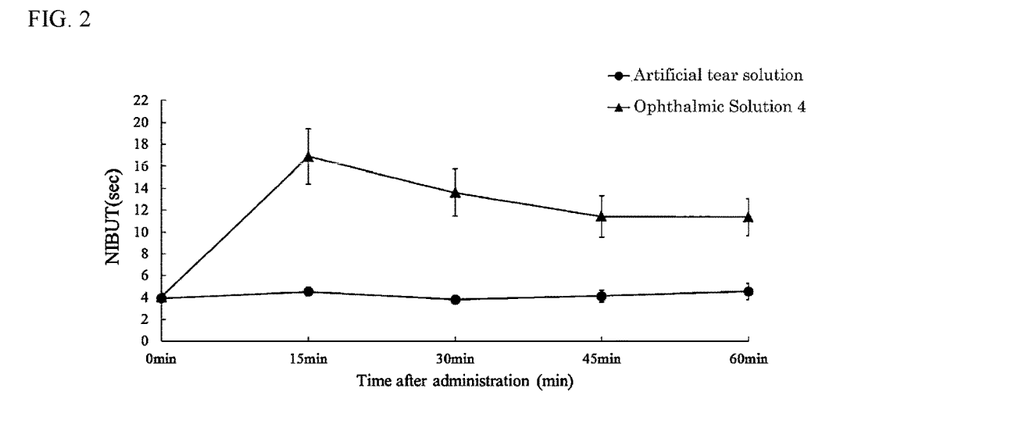
FIG. 2 is a graph showing the results of an Evaluation Test 1 of NIBUT increasing effect in Test Example 4.

The test results are shown in FIG. 2. As is clear from FIG. 2, when Ophthalmic Solution 4 was applied to the eyes wearing soft contact lenses, significant increases in NIBUT were observed in comparison with prior to application at all measurement points up to 60 minutes after application. On the other hand, increases in NIBUT were not observed in eyes applied with the artificial tear solution.

(Discussion)

On the basis of the above results, the present ophthalmic solution was shown to improve decreases in tear film stability caused by wearing soft contact lenses. This effect of the present ophthalmic solution was prominent even when compared with an artificial tear solution typically used for the treatment of dry eye. Accordingly, the present ophthalmic solution is useful for the prevention and/or treatment of dry eye in an eye wearing a soft contact lens. In addition, the present ophthalmic solution is also useful for the prevention and/or treatment of eye dryness and/or eye discomfort in an eye wearing a soft contact lens.

Test Example 5

Evaluation Test of NIBUT Increasing Effect 2

The NIBUT values of a diquafosol ophthalmic solution were examined in eyes in which tear film stability had decreased as a result of wearing soft contact lenses.

(Sample Preparation)

Ophthalmic Solution 4 was prepared in the same manner as Ophthalmic Solution 1 in accordance with the formulation shown in Table 1.

(Test Method)

NIBUT values before and 5, 15, 30, 45 and 60 minutes after applying Ophthalmic Solution 4 (20 μl/eye) were measured for the eyes of cynomolgus monkeys wearing soft contact lenses (product name: Menicon Soft MA®) with a dry eye observation system (DR-1, Kowa Co., Ltd.). An artificial tear solution (product name: Soft Santia®) and sodium hyaluronate (product name: Hyalein® Mini Ophthalmic Solution 0.1%) was used as controls (N=11 eyes).

(Results)

Figure 3:
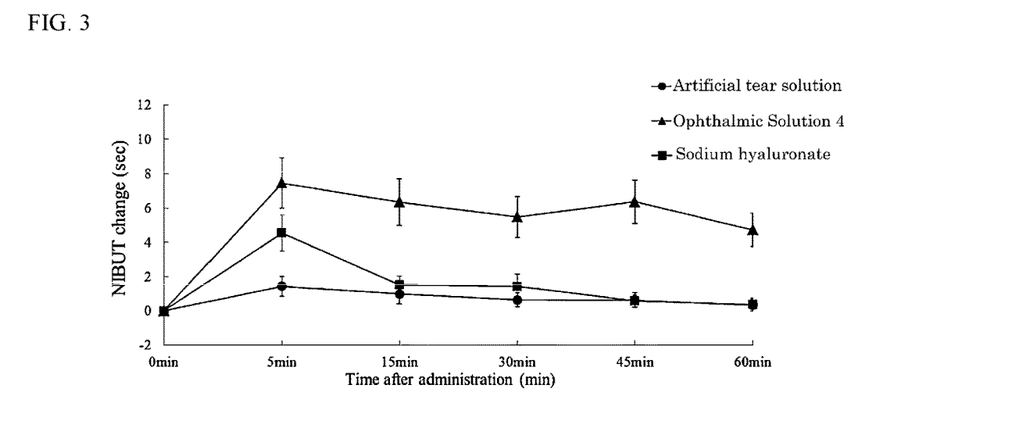
FIG. 3 is a graph showing the results of an Evaluation Test 2 of NIBUT increasing effect in Test Example 5.

The test results are shown in FIG. 3. As is clear from FIG. 3, when Ophthalmic Solution 4 was applied to the eyes wearing soft contact lenses, significant increases in NIBUT were observed in comparison with prior to application at all measurement points up to 60 minutes after application. On the other hand, increases in NIBUT were not observed in eyes applied with the artificial tear solution. In addition, although an increase in NIBUT was observed 5 minutes after application in eyes administered sodium hyaluronate, the increasing effect thereof was lower than that of Ophthalmic Solution 4 and increases in NIBUT were not observed at 15 minutes after application and beyond.

(Discussion)

On the basis of the above results, the present ophthalmic solution was shown to improve decreases in tear film stability caused by wearing soft contact lenses. This effect of the present ophthalmic solution was prominent even when compared with an artificial tear solution and a sodium hyaluronate ophthalmic solution typically used for the treatment of dry eye. Accordingly, the present ophthalmic solution is useful for the prevention and/or treatment of dry eye in an eye wearing a soft contact lens. In addition, the present ophthalmic solution is also useful for the prevention and/or treatment of eye dryness and/or eye discomfort in an eye wearing a soft contact lens.

Test Example 6

Comparative Test of NIBUT Increasing Effect

A comparative study of NIBUT values was conducted between the present ophthalmic solution and an ophthalmic solution comprising BAK (ophthalmic solution comprising diquafosol sodium and BAK) in eyes in which tear film stability had decreased as a result of wearing soft contact lenses.

(Sample Preparation)

Ophthalmic Solution 4 was prepared in the same manner as Ophthalmic Solution 1 in accordance with the formulation shown in Table 1.

In addition, Ophthalmic Solution 11 comprising BAK instead of the chlorhexidine gluconate of Ophthalmic Solution 4 was prepared for use as a comparative example. More specifically, diquafosol sodium (3 g), sodium hydrogen phosphate hydrate (0.2 g), sodium chloride (0.41 g), potassium chloride (0.15 g) and BAK (0.0075 g) were dissolved in water and brought to a final volume of 100 mL followed by the addition of a pH adjuster to the adjust the pH to 7.5. Ophthalmic Solution 4 and Ophthalmic Solution 11 are ophthalmic solutions that both comprise the same concentrations of active ingredient (diquafosol sodium). In addition, Ophthalmic Solution 4 and Ophthalmic Solution 11 are ophthalmic solutions that both comply with the preservative effectiveness test standards of the Japanese Pharmacopoeia and have equivalent preservative effectiveness.

(Test Method)

NIBUT values before and 30 minutes after applying Ophthalmic Solution 4 or Ophthalmic Solution 11 (20 μl/eye) were measured for the eyes of cynomolgus monkeys wearing soft contact lenses (product name: Menicon Soft MA®) with a dry eye observation system (DR-1, Kowa Co., Ltd.) (N=11 eyes).

(Results)

The test results are shown in Table 7.

TABLE 7

|  | Ophthalmic Solution 4 | Ophthalmic Solution 11 |
| --- | --- | --- |
| NIBUT before application (sec) | 3.40 | 3.39 |
| NIBUT 30 minutes after application (sec) | 8.20 | 6.25 |

As a result of measuring and comparing NIBUT values before and 30 minutes after applying the present ophthalmic solution (Ophthalmic Solution 4) or a BAK-comprising ophthalmic solution (Ophthalmic Solution 11), which comply with the preservative effectiveness test standards of the Japanese Pharmacopoeia and have equivalent preservative effectiveness, the present ophthalmic solution was shown to have higher NIBUT increasing effect than the BAK-comprising ophthalmic solution.

(Discussion)

Based on the above results, the present ophthalmic solution was shown to improve decreases in tear film stability caused by wearing soft contact lenses to a greater degree than an ophthalmic solution comprising BAK.

Preparation Examples

Although the following provides a more detailed explanation of preparations of the present invention by indicating examples thereof, the present invention is not limited to these preparation examples.

(Formulation Example 1

Ophthalmic Solution (3% (w/v))

| In 100 ml | |
| --- | --- |
| Diquafosol sodium | 3 g |
| Sodium hydrogen phosphate hydrate | 0.1-0.5 g |
| Sodium chloride | 0.01-1 g |
| Potassium chloride | 0.01-1 g |
| Sodium edetate hydrate | 0.0001-0.1 g |
| Chlorhexidine gluconate | 0.0001-0.1 g |
| Sterile purified water | q.s. |

Diquafosol sodium and other ingredients listed above are added to sterile purified water and they are mixed sufficiently so that this ophthalmic solution can be prepared.

(Formulation Example 2

Ophthalmic Solution (3% (w/v))

| In 100 ml | |
| --- | --- |
| Diguasofol sodium | 3 g |
| Sodium hydrogen phosphate hydrate | 0.1-0.5 g |
| Sodium chloride | 0.01-1 g |
| Potassium chloride | 0.01-1 g |
| Sodium edetate hydrate | 0.0001-0.1 g |
| Chlorhexidine gluconate | 0.0001-0.1 g |
| Polysorbate 80 | 0.0001-0.1 g |
| Sterile purified water | q.s. |

Diquafosol sodium and other ingredients listed above are added to sterile purified water and they are mixed sufficiently so that this ophthalmic solution can be prepared.

INDUSTRIAL APPLICABILITY

The present ophthalmic solution has superior preservative effectiveness. Moreover, since the present ophthalmic solution prevents deformation of soft contact lenses, it can also be used for soft content lenses. In addition, the present ophthalmic solution demonstrates higher cell viability in cultured immortalized human corneal epithelial cells than ophthalmic solutions comprising BAK and ophthalmic solutions comprising chlorhexidine but not comprising diquafosol or a salt thereof. Accordingly, the present ophthalmic solution is highly safe with respect to a living body, and particularly keratoconjunctival epithelium, and is useful for diseases such as dry eye in which keratoconjunctival epithelium is unstable. In addition, the present ophthalmic solution significantly increases NIBUT in an eye wearing a soft contact lens. On the other hand, this effect is not observed with artificial tear solutions. Namely, the present ophthalmic solution stabilizes the tear film in an eye wearing a soft contact lens. Since the onset and/or exacerbation of dry eye symptoms caused by wearing soft contact lenses is attributable to a decrease in tear film stability, stabilization of the tear film by the present ophthalmic solution is useful for the prevention and/or treatment of dry eye in an eye wearing a soft contact lens. In addition, the present ophthalmic solution is also useful for the prevention and/or treatment of eye dryness and/or eye discomfort in an eye wearing a soft contact lens.

The invention claimed is:

1. An aqueous ophthalmic solution comprising diquafosol or a salt thereof at a concentration of 0.1% to 10% (w/v) and a chlorhexidine at a concentration of 0.002% to 0.005% (w/v).

2. The aqueous ophthalmic solution accoriding to claim 1, wherein the chlorhexidine is chlorhexidine gluconate.

3. The aqueous ophthalmic solution according to claim 1, wherein the concentration of diquafosol or a salt thereof in the ophthalmic solution is 3% (w/v).

4. The aqueous ophthalmic solution according to claim 1, further comprising a chelating agent.

5. The aqueous ophthalmic solution according to claim 4, wherein the chelating agent is edetic acid or a salt thereof.

6. The aqueous ophthalmic solution according to claim 1, wherein the ophthalmic solution for a soft contact lens.

7. The aqueous ophthalmic solution according to claim 6, wherein the soft contact lens is a silicone hydrogel contact lens.

8. A method for preventing deformation of a soft contact lens comprising immersing the soft contact lens in the aqueous ophthalmic solution according to claim 1.

9. The aqueous ophthalmic solution according to claim 1, wherein the ophthalmic solution is for the prevention and/or treatment of dry eye in an eye wearing a soft contact lens.

10. The aqueous ophthalmic solution according to claim 1, wherein the ophthalmic solution is for improving tear film stability in an eye wearing soft contact lens.

11. The aqueous ophthalmic solution according to claim 1, wherein the ophthalmic solution is for the prevention or treatment of eye dryness or eye discomfort in an eye wearing a soft contact lens.

12. The aqueous ophthalmic solution according to claim 9, wherein the soft contact lens is a silicone hydrogel contact lens.

* * * * *